United States Patent [19]

Utz

[11] Patent Number: 4,832,027

[45] Date of Patent: May 23, 1989

[54] SURGICAL CLAMP

[76] Inventor: Alice Utz, Larchenring 19, CH-7270 Davos, Switzerland

[21] Appl. No.: 22,635

[22] PCT Filed: May 23, 1986

[86] PCT No.: PCT/CH86/00067

§ 371 Date: Mar. 16, 1987

§ 102(e) Date: Mar. 16, 1987

[87] PCT Pub. No.: WO86/06952

PCT Pub. Date: Dec. 4, 1986

[30] Foreign Application Priority Data

May 31, 1985 [CH] Switzerland ............... 2307/85

[51] Int. Cl.⁴ .................................. A61B 17/08
[52] U.S. Cl. ............................. 126/337; 128/346
[58] Field of Search ............... 128/337, 335, 346, 330

[56] References Cited

U.S. PATENT DOCUMENTS

| 1,644,625 | 10/1927 | Babain | 128/346 |
| 3,385,299 | 5/1968 | LeRoy | 128/346 |
| 3,598,125 | 8/1971 | Cogley | 128/346 |
| 3,601,727 | 8/1971 | Finegold | 128/337 |
| 4,217,902 | 8/1980 | March | 128/337 |
| 4,535,742 | 8/1985 | Sheehan | 128/335 |
| 4,681,109 | 7/1987 | Arroyo | 128/335 |

FOREIGN PATENT DOCUMENTS

| 419096 | 12/1910 | France | 128/346 |
| 709422 | 8/1931 | France | 128/346 |
| 1324556 | 3/1963 | France | 128/346 |
| 456458 | 11/1936 | United Kingdom | 128/346 |

Primary Examiner—Carl Stuart Miller
Attorney, Agent, or Firm—Thomas W. Speckman

[57] ABSTRACT

To obtain better cosmetic results after surgical operations and to reduce scarring and eliminate the infection risks of suturing holes, a spring actuated clamp (1) having compression surfaces (5') with flat or rounded protuberant parts (7) is provided. The surgical clamp prevents perforations of the skin and at the same time provides for a good securing of the clamp to the skin.

17 Claims, 3 Drawing Sheets

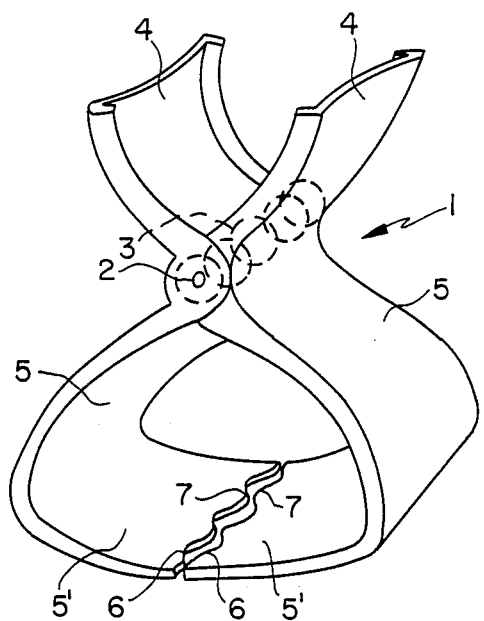
FIG. 1
FIG. 2
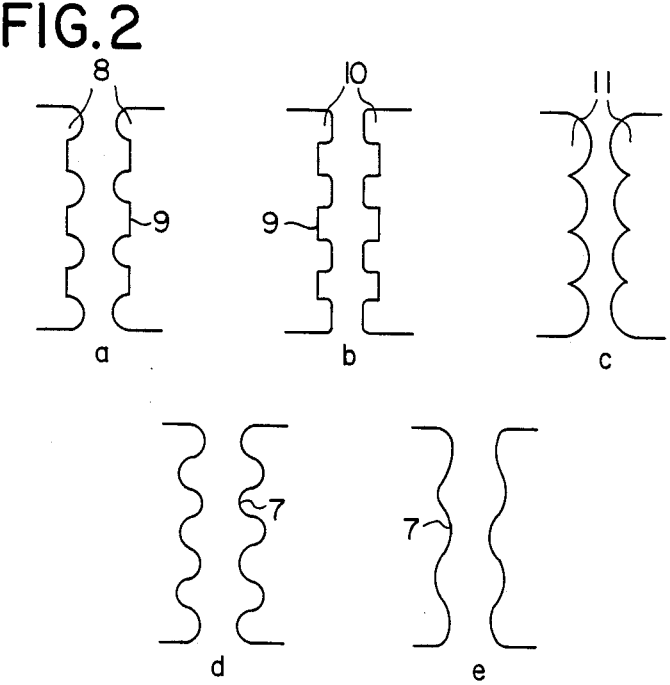

SURGICAL CLAMP

BACKGROUND OF THE INVENTION

Field of the Invention

After every surgical operation, the healing of the wound has great importance. Attempts have therefore been made to create the optimal preconditions for the most risk-free, painless, and rapid healing. It is known that wounds, the cutting edges of which have been held together by means of clamps or threads, heal more rapidly and cosmetically more attractively than wounds which are allowed to heal by themselves (Williams and Harrison, 1977). In many specialties of medicine, clamping techniques have their fixed place next to suture techniques, particularly in gynecological and abdominal operations. Recently, clamping techniques have again found increasing application in various other fields. These offer many technical and medical advantages in comparison with suture techniques. During their application the rates of infection are lower, granulomas do not arise as frequently, and the average hospital stay of the patient is thus shorter (Beresford et al, 1984). In the case of dermal inflammations, clamping is therefore preferred, because it is much faster than the application of a thread suture. The skin transplant can be placed more rapidly, and the critical anesthesia time can therefore be reduced (Kahn et al, 1984; Hallock et al, 1984). Stephens and Niesche (1974) recommend skin clamping for wound closures during abdominal operations, neck operations, breast and thorax operations, and Nockemann (1968) recommends it for skin closures after thyroid operations. According to Swanson (1982), clamping is suited on the scalp, on the face, and on the extremities. Through the traumatization of the tissue, which is reduced in comparison with thread suturing, clamping provides a more attractive healing of the wound and a slighter formation of scars. According to Nockemann (1965/1968), sutures leave scars at the puncture points, as well as at the points where the thread has been laced or compressed with the tissue for a period of time. These scars can be very irritating to the skin, and have unattractive effects. Attempts have therefore been made to keep the size and number of puncture points as small as possible and to entirely avoid lines of scar tissue pressure points, which are caused by the thread, and which produce the known Strickleiter syndrome.

These attempts led to the closure of wounds of the skin by means of clamps. Their application and removal is simple and fast. In addition, the danger of bacterial colonization on the metal of the clamps is slight, since the germs adhere poorly to the smooth surface, and the metal furthermore has its own, germ-killing, bactericidal effect. In contrast to this, the use of suture materials in the wound increases the risk of the virulence of the staphylococci by some 10,000-fold. The abscess rate is about three times less with the clamping technique. According to Stephens (1970), wounds closed with clamps showed, on the 7th post-operative day, better mechanical properties than those closed by means of a suture thread; that is, the coefficient of elasticity is greater, the breaking strength is higher, and the capacity for energy absorption without rupture is better. Lowdon et al (1980) also found that the post-operative complications in the form of anastomosis weakness, wound infections, and hemorrhages were about 25% rarer when using clamps. An experiment by Meiring (et al, 1982) on each of 20 patients also showed, that the wound closure by means of clamping was about 80% faster, and could also be carried out more simply, than was the case with a conventional threaded suture.

These numerous and evident advantages show the fundamental significance of the clamping technique, which has been used in place of suture techniques in most clinics in the USA. Nevertheless, the clamps most commonly used today still have decisive defects, which must be eliminated.

DESCRIPTION OF THE PRIOR ART

Conventional clamps for application to all parts of the body, with the exception of the scalp, without exception puncture both sides of the skin on the wound to be held together, and at several places. For one thing, this puncturing is painful for the patient, and, for another, it is undesirable for medical reasons. In addition to cosmetic disadvantages from the punctures, these above all else increase the danger of infection, since foreign material penetrates into the wound. Furthermore, the removal of the clamps requires, in many clamping systems, a special device, which is not structured simply and is therefore time-consuming.

A skin clamp is already known in the technical trade, which does not puncture the parts of the skin which are to be held together. This clamp is only used in neurosurgery, for trepanation. It is only used temporarily, that is, only for the crude clamping away of the blood vessels during the operation, since, in neurosurgery, massive blood losses must be taken into account. This clamping away squeezes and traumatizes the skin very badly, but the loss of blood can be restricted in this way. This clamp thus differs from the wound clamp in accordance with the invention, both as to function and operational goals. Furthermore, it can, for the reasons stated above, only be used during the operation, and not afterwards, such as, for example, for closure of the wound. It can only, because of its construction, only be applied to the scalp, since it only allows a very slight spreading, and therefore can only be used where the subcutaneous layer is very thin, and lies directly on the bone (skull).

Furthermore, this skin clamp, for application as well as for removal, must be operated by means of special tongs. The compression edges of this scalp clamp are formed in a corrugated manner, so that one convexity of the shaft fits into the convexity of the opposing side. This causes traction and compression forces on the skin, which work in different directions, and, when left for longer periods on the skin, can leave behind scar-like traces.

SUMMARY OF THE INVENTION

It is the goal of the present invention to eliminate the stated disadvantages of the conventional clamps while maintaining the fundamental advantages of the clamping technique, and to create a skin clamp, which can be applied to all parts of the body simply and without puncturing the skin.

This task is, in accordance with the invention, solved by means of a wound clamp comprising two clamp parts movable relative to one another, each clamp part having a handle, with the handles compressible toward one another to open the clamp. Each clamp part has a claping surface, and the clamping surfaces are aligned with and directed toward one another. Each clamping surface is provided with corrugated compression edges, with the protuberant parts of the clamping blade corrugated edges aligned with one another.

Exemplary embodiments of the wound clamp with the invention are depicted in the following diagrams, which, for the sake of clarity, are shown on an enlarged scale. These show the following:

FIG. 1: a perspective view of a wound clamp having two parts which can be pivoted against one another;

FIG. 2a-2e advantageous formations of the compression edges of the clamp parts;

FIG. 3: a perspective view of two displaceable clamp parts;

FIG. 4: a frontal view of a clamp comprising a flat spring constructed from the wound clamp parts from FIG. 3;

FIG. 5: a front view of a clamp comprising a compression spring and the clamp parts shown in FIG. 3;

FIG. 6: a front view of a clamp comprising a tension spring and the clamp parts shown in FIG. 3;

FIG. 7: a perspective view of a wound clamp comprising a driving rod.

DESCRIPTION OF PREFERRED EMBODIMENTS

Figure 3:
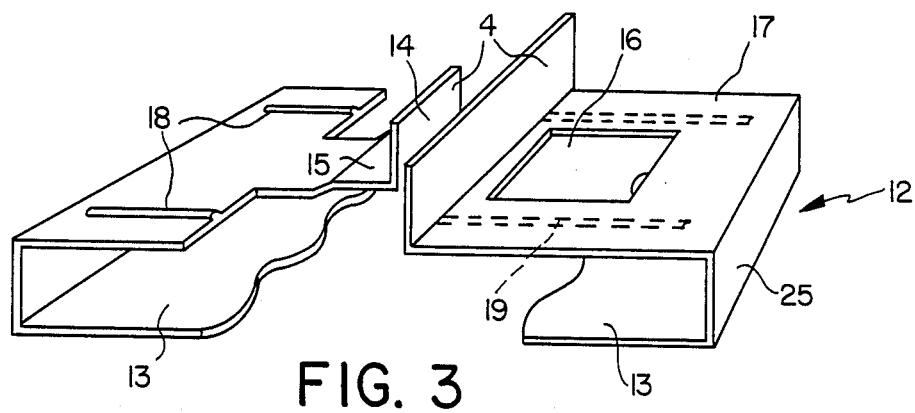

The embodiment of the wound clamp shown in FIG. 1 is constructed according to the clothespin principle, that is, both clamp parts (1) are positioned to pivot with respect to one another on a common axis (2). A torsion spring (3), which is provided around the axis (2), presses the sides of the clamp parts (1), which are formed as handles, away from one another, and thus correspondingly presses the clamping blades (5) against one another. This construction permits, through the application of the law of leverage, a large spreading of the clamping blades (5), with comparatively smaller swivelling of the handles (4). Furthermore, the handles (4) can be held with just two fingers, and the clamp is therefore simple to operate. The compression edges (6) of the clamping blades (5), which are intended to come into contact with the skin are, in this embodiment, formed in a corrugated manner. The corrugation peaks (7) of the compression edges which oppose one another are aligned opposite. The roundings of the corrugation peaks prevent, on the one hand, a puncturing of the skin, and, on the other, they increase the specific pressure on the skin, and thereby improve the adhesion of the applied clamp in comparison with straight edges. A further advantage of this embodiment consists of the fact that the clamp for post-operative swellings in the area of the suture of the wound allows sufficient space above the compression edges. There are clamp systems in which this is not the case, and which therefore leave traces in the scar, which are known under the name of "Strickleiter syndrome". The clamp blades (5) extend from the axis (2) in a curved line externally. In the lowest area, the clamp blades are angled at about 90° inwardly, so that the clamping blade surfaces (5') lie in a plane with the clamping blade. This plane touches the skin somewhat tangentially. The compression edges (6) of the clamping blade surfaces (5') thereby move the wound edges roughly parallel to the surface of the skin.

In FIG. 2, further examples of advantageous compression edges (6) on the clamping blades (5) are shown. All these embodiments are so constructed that they never puncture the skin, but nonetheless guarantee a satisfactory adhesion of the clamp to the skin, so that only the epithelial layer of the skin, at the most, is ever traumatized.

FIG. (2a) shows compression edges with semi-circular peaks (8) facing one another, which have a specific distance (9) from one another. In FIG. (2b), the compression edges have short, straight protuberant parts (10) with rounded corners, which are likewise positioned at a certain distance (9) from each other. In FIG. (2c), the protuberant parts are formed by circular segments (11), which are arranged in rows in series with each other. The arrangements in FIGS. (2d) and (2e) show protuberant parts, which are formed by corrugated peaks (7) of shafts with varying radii of curvature.

In FIG. 3, two wound clamping parts (12) for a particularly flat wound clamp are shown in a perspective view. Both parts consist of perforated plates, from which clamping surfaces are formed by two separate rectangular surfaces extending toward one another while, on the other end of the wound clamp parts (12), handles are set vertical to the clamping surfaces (13). The one handle (14) is thus narrower, and is formed as a tab, which, through the shifting of its foot unit (15) around a metal plate thickness upwardly, fits into a corresponding aperture (16) in the other clamping part (17), where it locates easily, particularly when guides (18) provided on one clamp part, are inserted into the corresponding grooves (19) provided on the other clamp part. If the handles (4) are now pressed toward one another, then the clamping surfaces shift in a plane parallel to one another.

Figure 4:
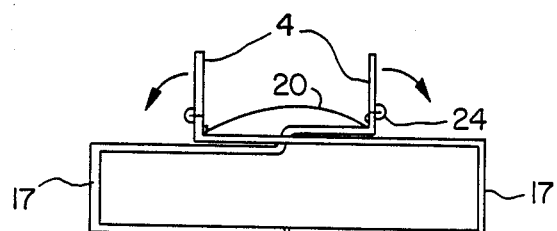
Figure 5:
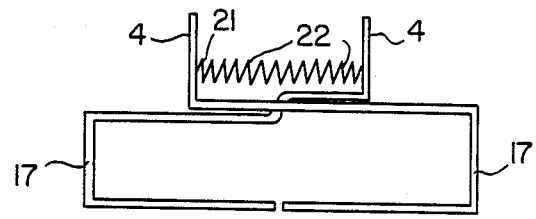

A flat spring (20) inserted between the handles (4) ensures, in accordance with the embodiment shown in FIG. 4, the closing of both the clamping surfaces, which presses these handles away from one another, and thereby presses the compression edges (6) against one another. In FIG. 5, this function is achieved by a compression spring (21), which, is mounted on pegs (22), which extend in a manner aligned with one another, and have about ⅓ of the length of the compression spring. The pressing together of the compression edges (6) can also be attained by means of a tension spring (23) suspended between the clamp parts (17).

Figure 6:
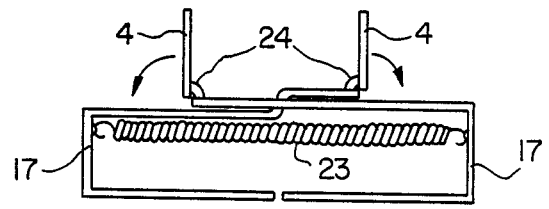

The handles (4) in FIG. 4 and FIG. 6 are moreover provided with hinges (24), which make possible a folding under of the handle (4) after the application of the wound clamp. The construction according to FIGS. 3 to 6 makes possible a particularly flat wound clamp. The side walls (25) of the rectangular clamp parts (12) must be high enough to afford space for a possible swelling of the wound. If the handles (14) are additionally also hingeable, the entire height of the clamp is, in relation to the width, particularly advantageous. This is of importance if a connection is applied over the clamps, but the pressure on the clamps is reduced, and there is also no danger of tipping from forces which are exerted by the connection on the clamp. At the same time, the specific contact pressure is also reduced by the size of the clamping surfaces (13) provided on both handles (4) which additionally give the applied wound clamp further stability as well. The parallel guidance of the clamping parts (17) helps the wound to only be pressed together at the skin surface, which facilitates a slighter degree of scar formation.

Figure 7:
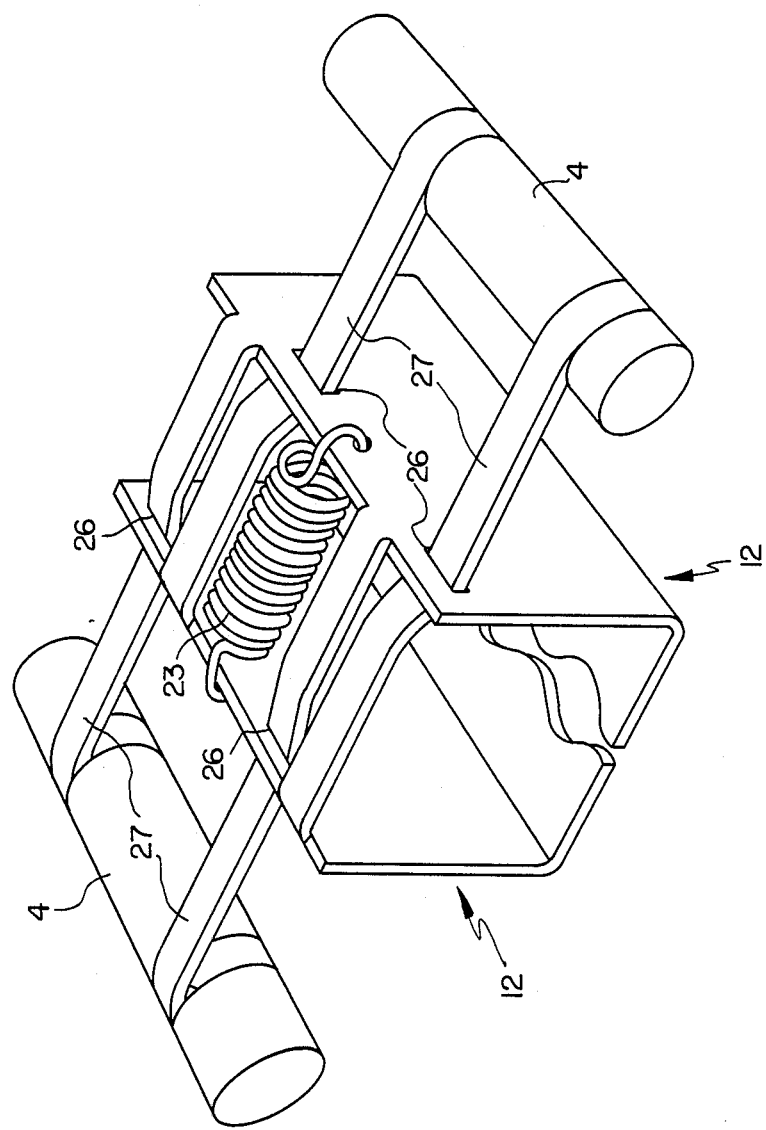

In FIG. 7, a particularly advantageous embodiment of the invention is depicted. The clamping parts (12) each have, parallel to the clamping device, two driving rods (27), which in the opposing clamping parts, are conducted through an aperture (26). This total of four apertures (26) gives the four driving rods (27) guidance, and ensures that, upon pressing the handle (4) attached to it together, the clamping parts (12) are pushed apart, parallel from one another. The handles (4) consist here of round steel units, around which the ends of the driving rods (27) are bent in a groove provided for the purpose. When the clamping parts (12) the pressed apart from one another, the torsion spring (23) suspended between these parts (12) is extended. The application of the wound clamp then follows by releasing the handles (4), so that both the clamping parts (12), by virtue of the tension spring (23), are pressed against one another.

The simple form makes possible a low-cost production and mounting of the clamp. These new wound clamps can also be made from inert stainless steel. The use of other materials, such as, for example, plastics, is possible.

Many advantages are connected with the fact that this new skin clamp does not puncture the skin at any place. First of all, the pain for the patient is considerably reduced; secondly, a cosmetically superior result is attained, since no permanent puncture points or scarring from puncture points appear. For medical reasons, the substantially lower danger of infection is important, since it is thereby ensured that foreign material now only comes in contact with the surface of the skin, and no longer comes in contact with the tissue and the wound. As a further advantage relative to different conventional clamping systems, there should be mentioned the fact that, because of the construction of the new skin clamp, space remains for the tissue to expand in event of possible post-operative swelling. Since the wound clamp in accordance with the invention can be spread very far apart, its application to all parts of the body is possible. Its application, as well as its removal, is accomplished by means of just two fingers, and without the use of auxilliary instruments.

I claim:

1. A wound clamp for holding together the edges of wounds during the healing process comprising:
    two clamp parts (12) which are movable relative to one another, each said clamp part having a handle (4), said handles (4) movable toward one another to open said wound clamp, said clamping parts (12) each having a clamping surface (13), said clamping surfaces (13) extending in the same plane and directed toward one another, said clamping surfaces (13) having corrugated terminal compression edges with protuberant portions of said compression edges aligned with and opposite one another;
    corresponding elements of said clamp parts movable in a parallel-displaceable manner relative to one another in said plane, and a spring is provided whereby said movement of said clamp parts toward one another in at least one direction is spring actuated; and
    each said clamping part (12) having two driving rods (27) positioned in parallel, each said driving rod conducted through an aperture (26) in the other wound clamping part, said handles being attached at the ends of said driving rods and said spring comprising a tension spring.

2. A wound clamp for holding together the edges of wounds during the healing process comprising:
    two clamp parts (12) which are movable relative to one another, each said clamp part having a handle (4), said handles (4) movable toward one another to open said wound clamp, said clamping parts (12) each having a clamping surface (13), said clamping surfaces (13) extending in the same plane and directed toward one another, said clamping surfaces (13) having corrugated terminal compression edges with protuberant portions of said compression edges aligned with and opposite one another;
    corresponding elements of said clamp parts movable in a parallel-displaceable manner relative to one another in said plane, and a spring is provided whereby said movement of said clamp parts toward one another in at least one direction is spring actuated; and
    said spring comprising a tension spring (21) which draws said clamping parts (12) toward each other.

3. A wound clamp for holding together the edges of wounds during the healing process comprising:
    two clamp parts (12) which are movable relative to one another, each said clamp part having a handle (4), said handles (4) movable toward one another to open said wound clamp, said clamping parts (12) each having a clamping surface (13), said clamping surfaces (13) extending in the same plane and directed toward one another, said clamping surfaces (13) having corrugated terminal compression edges with protuberant portions of said compression edges aligned with and opposite one another;
    said clamping parts (12) being provided with at least one locking device, whereby said protuberant portions of said corrugated compression edges are spaced in a closed position of said clamp.

4. A wound clamp in accordance with claim 3, wherein corresponding elements of said clamp parts are movable in a parallel-displaceable manner relative to one another in said plane, and a spring is provided whereby said movement of said clamp parts toward one another in at least one direction is spring actuated.

5. A wound clamp for holding together the edges of wounds during the healing process comprising: two clamp parts (12) which are movable relative to one another, each said clamp part having a handle (4), said handles (4) movable toward one another to open said wound clamp, said clamping parts (12) each having a clamping surface (13), said clamping surfaces (13) extending in the same plane and directed toward one another, and said clamping surfaces (13) having corrugated terminal compression edges with rounded protuberant portions of said compression edges aligned with and opposite one another.

6. A wound clamp for holding together the edges of wounds during the healing process comprising:
    two clamp parts (12) which are movable relative to one another, each said clamp part having a handle (4), said handles (4) movable toward one another to open said wound clamp, said clamping parts (12) each having a clamping surface (13), said clamping surfaces (13) extending in the same plane and directed toward one another, said clamping surface (13) having corrugated terminal compression edges with protuberant portions of said compression edges aligned with and opposite one another;
    corresponding elements of said clamp parts movable in a parallel-displaceable manner relative to one another in said plane, and a spring is provided whereby said movement of said clamp parts toward one another in at least one direction is spring actuated; and
    each said clamping part (12) being formed by an L-shaped metal sheet, one leg of said L forming said clamping surface (13) and the other leg of said L forming a side wall, said side wall having two apertures (26) providing guidance for driving rods (27).

7. A wound clamp in accordance with claim 5, wherein said clamping parts are pivotable with respect to one another around a common pivot axis (2), and a torsion spring (3) is provided around said pivot axis.

8. A wound clamp in wherein said spring comprises a flat

9. A wound clamp in accordance with claim 4, wherein said spring comprises a compression spring, said handles (4) of the wound clamp are provided with pegs (22) aligned with and extending toward one another, and said spring is retained on on said pegs (22).

10. A wound clamp in accordance with claim 3, wherein said handles (4) are provided with hinges (24) whereby said handles are pivotable.

11. A wound clamp in accordance with claim 3, wherein said locking device is adjustable as to said spaced width.

12. A wound clamp in accordance with claim 3, wherein said protuberant parts of said corrugated terminal compression edges are generally rectangular.

13. A wound clamp in accordance with claim 6, wherein said handles (4) are attached at the end of said driving rods (27) and said movement is actuated by a tension spring (23).

14. A wound clamp in accordance with claim 13, wherein said driving rods (27) are formed by bars folded perpendicular from upper portions of each said side wall of said clamping parts (12).

15. A wound clamp in accordance with claim 14, wherein said bars have curved portions which cannot pass said apertures thereby forming locking means maintaining said protuberant portions of opposite said compression edges spaced in a closed position of said clamp.

16. A wound clamp in accordance with claim 6, wherein said driving rods (27) are formed by bars folded perpendicular from upper portions of each said side wall of said clamping parts (12).

17. A wound clamp in accordance with claim 16, wherein said bars have curved portions which cannot pass said apertures thereby forming locking means maintaining said protuberant portions of opposite said compression edges spaced in a closed position of said clamp.

* * * * *